United States Patent
Koizumi et al.

(10) Patent No.: US 9,826,209 B2
(45) Date of Patent: Nov. 21, 2017

(54) MEDICAL SYSTEM, METHOD FOR PERFORMING IMAGE PROCESSING SETTING OF MEDICAL SYSTEM, AND IMAGE PROCESSING DEVICE

(71) Applicant: OLYMPUS CORPORATION, Hachioji-shi, Tokyo (JP)

(72) Inventors: Yugo Koizumi, Yokohama (JP); Kyoko Honda, Tokyo (JP); Mai Ojima, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/266,566

(22) Filed: Sep. 15, 2016

(65) Prior Publication Data

US 2017/0006271 A1 Jan. 5, 2017

Related U.S. Application Data

(63) Continuation of application No. PCT/JP2015/066623, filed on Jun. 9, 2015.

(30) Foreign Application Priority Data

Jun. 16, 2014 (JP) ................. 2014-123535

(51) Int. Cl.
- *H04N 9/64* (2006.01)
- *H04N 9/73* (2006.01)

(Continued)

(52) U.S. Cl.
CPC .......... *H04N 9/735* (2013.01); *A61B 1/0002* (2013.01); *A61B 1/00009* (2013.01);
(Continued)

(58) Field of Classification Search
CPC .................................................. H04N 1/6052
See application file for complete search history.

(56) References Cited

U.S. PATENT DOCUMENTS

| | | |
|---|---|---|
| 2001/0007468 A1 | 7/2001 | Sugimoto et al. |
| 2011/0069164 A1 | 3/2011 | Ozawa et al. |

FOREIGN PATENT DOCUMENTS

| | | | |
|---|---|---|---|
| JP | 2000-261821 A | 9/2000 | |
| JP | 2001-028709 A | 1/2001 | |

(Continued)

OTHER PUBLICATIONS

Sep. 1, 2015 International Search Report issued in Patent Application No. PCT/JP2015/066623.

(Continued)

*Primary Examiner* — Gary C Vieaux
(74) *Attorney, Agent, or Firm* — Oliff PLC

(57) ABSTRACT

A medical system includes a first storage that stores image information on an image that is obtained by an imaging device capturing an image of a reference subject and on which image processing is performed by a first processing device, a second storage that stores image information on an image that is obtained by the imaging device capturing an image of the reference subject and on which image processing is performed by a second processing device, a comparison unit that compares the image information stored in the first storage with the image information stored in the second storage, and a setting changing unit that changes an image processing setting of the second processing device on the basis of a result of the comparison, such that the image information stored in the second storage is identical or substantially identical to the image information stored in the first storage.

7 Claims, 11 Drawing Sheets

(51) Int. Cl.
  *A61B 1/04* (2006.01)
  *A61B 1/00* (2006.01)
  *A61B 1/06* (2006.01)
  *H04N 5/232* (2006.01)
  *H04N 1/60* (2006.01)
  *G06T 5/00* (2006.01)
  *G06T 5/50* (2006.01)
  *G06T 7/90* (2017.01)
  *H04N 5/225* (2006.01)

(52) U.S. Cl.
  CPC ............ *A61B 1/00011* (2013.01); *A61B 1/04* (2013.01); *A61B 1/06* (2013.01); *G06T 5/001* (2013.01); *G06T 5/50* (2013.01); *G06T 7/90* (2017.01); *H04N 1/6052* (2013.01); *H04N 5/23293* (2013.01); *G06T 2207/10068* (2013.01); *H04N 2005/2255* (2013.01)

(56) References Cited

FOREIGN PATENT DOCUMENTS

| | | | |
|---|---|---|---|
| JP | 2001-028747 | A | 1/2001 |
| JP | 2001-197484 | A | 7/2001 |
| JP | 2010-051633 | A | 3/2010 |
| JP | 2010-145474 | A | 7/2010 |
| JP | 2011-087910 | A | 5/2011 |

OTHER PUBLICATIONS

Sep. 1, 2015 Written Opinion issued in Patent Application No. PCT/JP2015/066623.

Apr. 5, 2016 Notice of Rejection issued in Japanese Patent Application No. 2016-501259.

May 31, 2016 Decision to Grant issued in Japanese Patent Application No. 2016-501259.

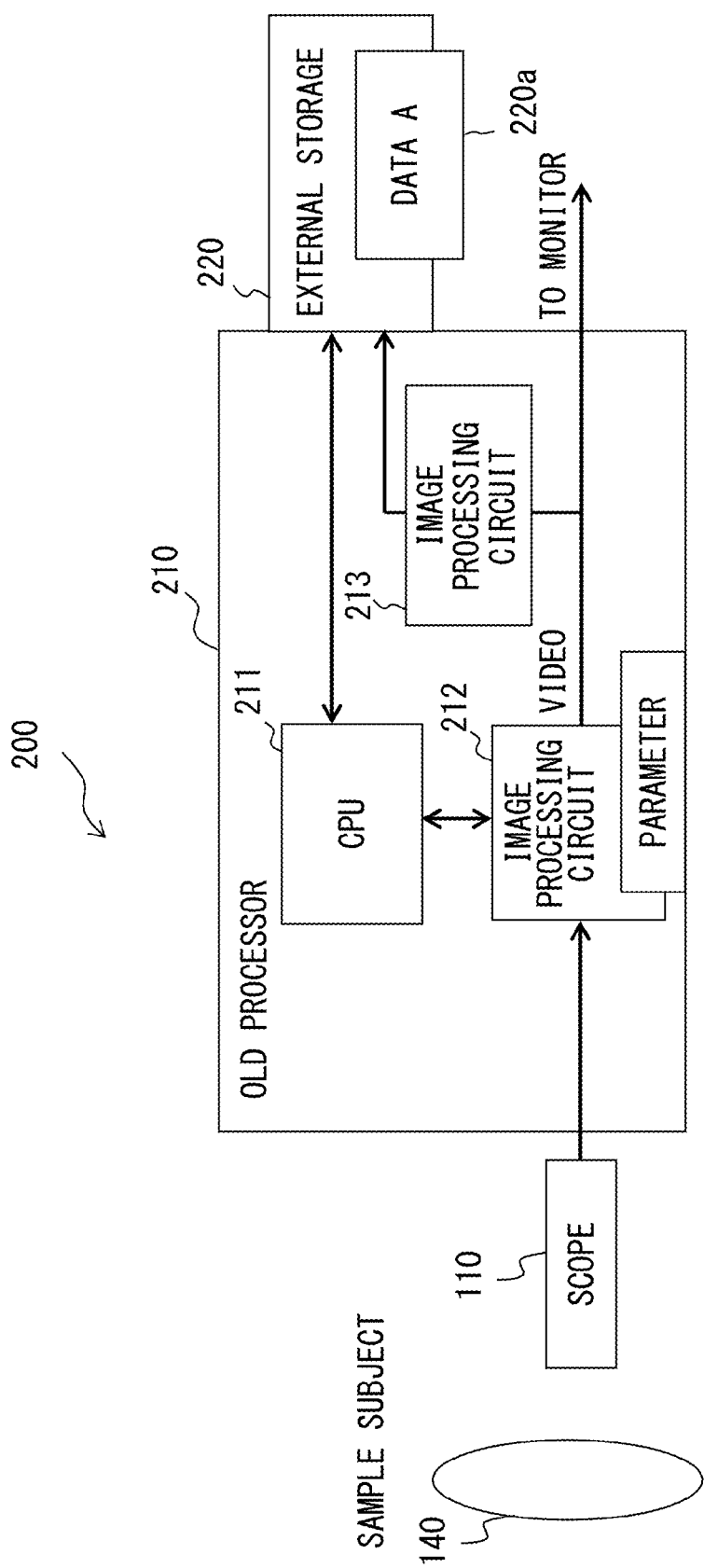
F I G. 5

MEDICAL SYSTEM, METHOD FOR PERFORMING IMAGE PROCESSING SETTING OF MEDICAL SYSTEM, AND IMAGE PROCESSING DEVICE

CROSS-REFERENCE TO RELATED APPLICATIONS

This application is based upon and claims the benefit of priority of the prior Japanese Patent Application No. 2014-123535, filed on Jun. 16, 2014, the entire contents of which are incorporated herein by reference.

This is a Continuation application of PCT Application No. PCT/JP2015/066623, filed on Jun. 9, 2015, which was not published under PCT Article 21(2) in English.

FIELD

The present invention relates to a medical system used in, for example, a medical institution, to a method for performing an image processing setting of the medical system, and to an image processing device.

BACKGROUND

Conventionally, as a medical system used in, for example, a medical institution, there exists an endoscopic system used in a hospital. The endoscopic system includes, for example, a scope (also referred to as an electronic endoscope), an image processing device (also referred to as a video processor), and a monitor, in which the image processing device performs image processing on an image captured by the scope and the image is displayed on the monitor.

The following system is known as an endoscopic system.

For example, an endoscopic system is known that uses an illumination light obtained by combining a fluorescent material and a light source, in which correction is performed such that an observation image always has the same color tone even if there exist individual differences in an optical property of an endoscope and in an optical property of a control device provided with the endoscope (see, for example, Japanese Laid-open Patent Publication No. 2011-87910). Further, for example, an electronic endoscopic system including a processor for an electronic endoscope is known that can easily confirm whether there exists an anomaly in color balance and that permits an easy determination of an anomalous portion (see, for example, Japanese Laid-open Patent Publication No. 2010-51633).

In an operation of an endoscopic system, a certain device provided in the system may be replaced with a device that is a relatively new model with respect to the certain device (that is, a new device). For example, the case of replacement purchase from an old image processing device to a new image processing device. In this case, a user (a doctor or a nurse) wants to use a new image processing device in a state in which the image processing setting of an old image processing device remains unchanged, such that he/she can also observe, after replacement, an image in a familiar color tone that is similar to before replacement.

SUMMARY

An aspect of the present invention provides a medical system that includes a first image processing device and a second image processing device that is different from the first image processing device, and an imaging device that is connected to the first image processing device or the second image processing device, the medical system including a first storage that stores image information on an image that is obtained by the imaging device capturing an image of a reference subject and on which image processing is performed by the first image processing device, a second storage that stores image information on an image that is obtained by the imaging device capturing an image of the reference subject and on which image processing is performed by the second image processing device, a comparison unit that compares the image information stored in the first storage with the image information stored in the second storage, and a setting changing unit that changes an image processing setting of the second image processing device on the basis of a result of the comparison performed by the comparison unit, such that the image information stored in the second storage is identical or substantially identical to the image information stored in the first storage.

Another aspect of the present invention provides a method for performing an image processing setting for a medical system that includes an imaging device that is connected to a first image processing device or a second image processing device that is different from the first image processing device, the method including a first image-capturing step of capturing, by the imaging device, an image of a reference subject, a first image-processing step of performing, by the first image processing device, image processing on the image captured by the imaging device, a first storing step of storing, in a first storage, image information on the image on which image processing is performed by the first image processing device and that is input to a display device, a second image-capturing step of capturing, by the imaging device, an image of the reference subject, a second image-processing step of performing, by the second image processing device, image processing on the image captured by the imaging device, a second storing step of storing, in a second storage, image information on the image on which image processing is performed by the second image processing device and that is input to the display device, a comparison step of comparing the image information stored in the first storage with the image information stored in the second storage, and a change step of changing an image processing setting of the second image processing device on the basis of a result of the comparison such that the image information stored in the second storage is identical or substantially identical to the image information stored in the first storage, wherein the second image-processing step, the second storing step, the comparison step, and the change step are performed repeatedly until a result of the comparison that the image information stored in the second storage and the image information stored in the first storage are identical or substantially identical is obtained.

Yet another aspect of the present invention provides an image processing device that includes a certain image processing unit that performs image processing on an image obtained by an imaging device capturing an image of a reference subject, a first storage that stores image information on an image that is obtained by the imaging device capturing an image of the reference subject and on which image processing is performed by another image processing unit that is different from the certain image processing unit, a second storage that stores image information on an image on which image processing is performed by the certain image processing unit, a comparison unit that compares the image information stored in the first storage with the image information stored in the second storage, and a setting changing unit that changes an image processing setting of the certain image processing unit such that the image information stored in the second storage is identical or substantially identical to the image information stored in the first storage.

BRIEF DESCRIPTION OF DRAWINGS

FIG. 5 is a diagram that illustrates an example of a configuration of an endoscopic system according to a second embodiment before replacement;

DESCRIPTION OF EMBODIMENTS

Embodiments will now be described with reference to the drawings.

First Embodiment

A medical system according to a first embodiment of the present invention is an endoscopic system.

The endoscopic system according to the present embodiment includes a new video processor and an old video processor that have a respective new and old relationship relative to each other as a video processor, and a scope and a monitor that are connected to the old video processor or the new video processor.

In an operation of the endoscopic system according to the present embodiment, the old video processor that is used along with the scope and the monitor is replaced with the new video processor due to, for example, a new purchase.

Figure 1:
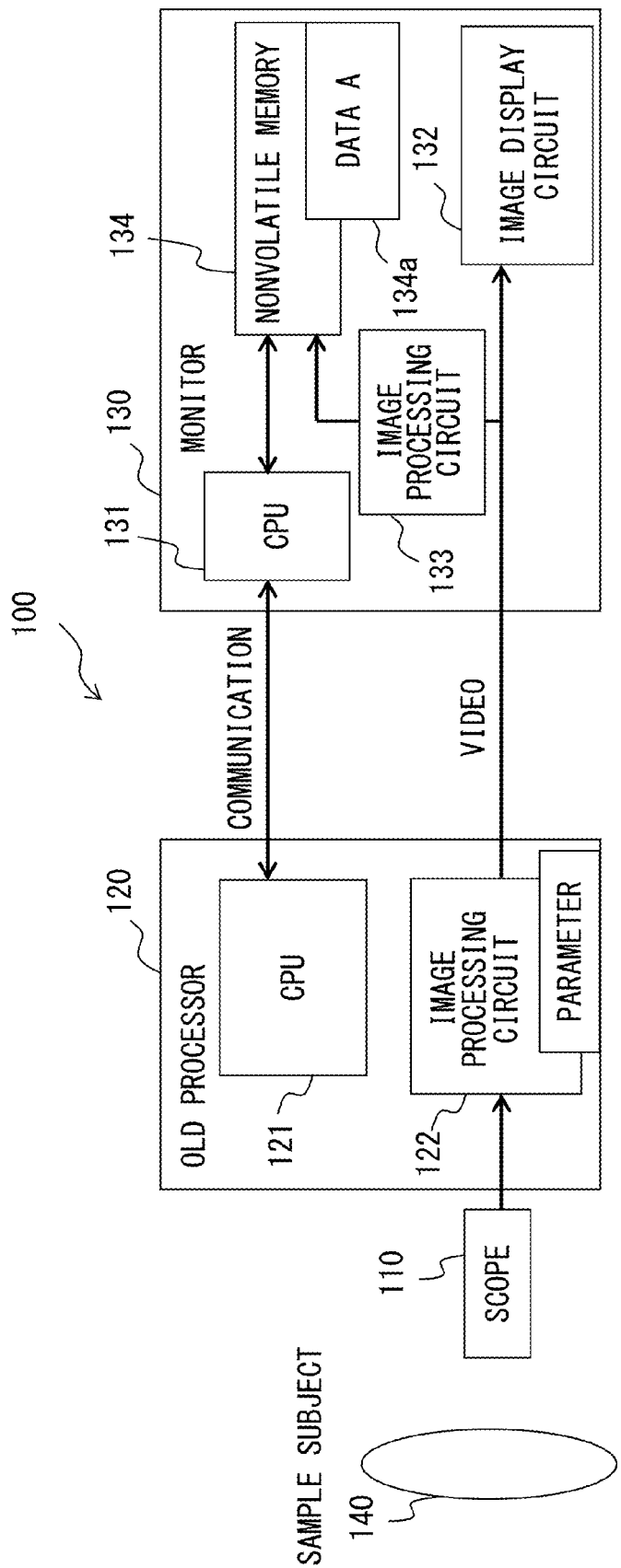
FIG. 1 is a diagram that illustrates an example of a configuration of an endoscopic system according to a first embodiment before replacement.
Figure 2:
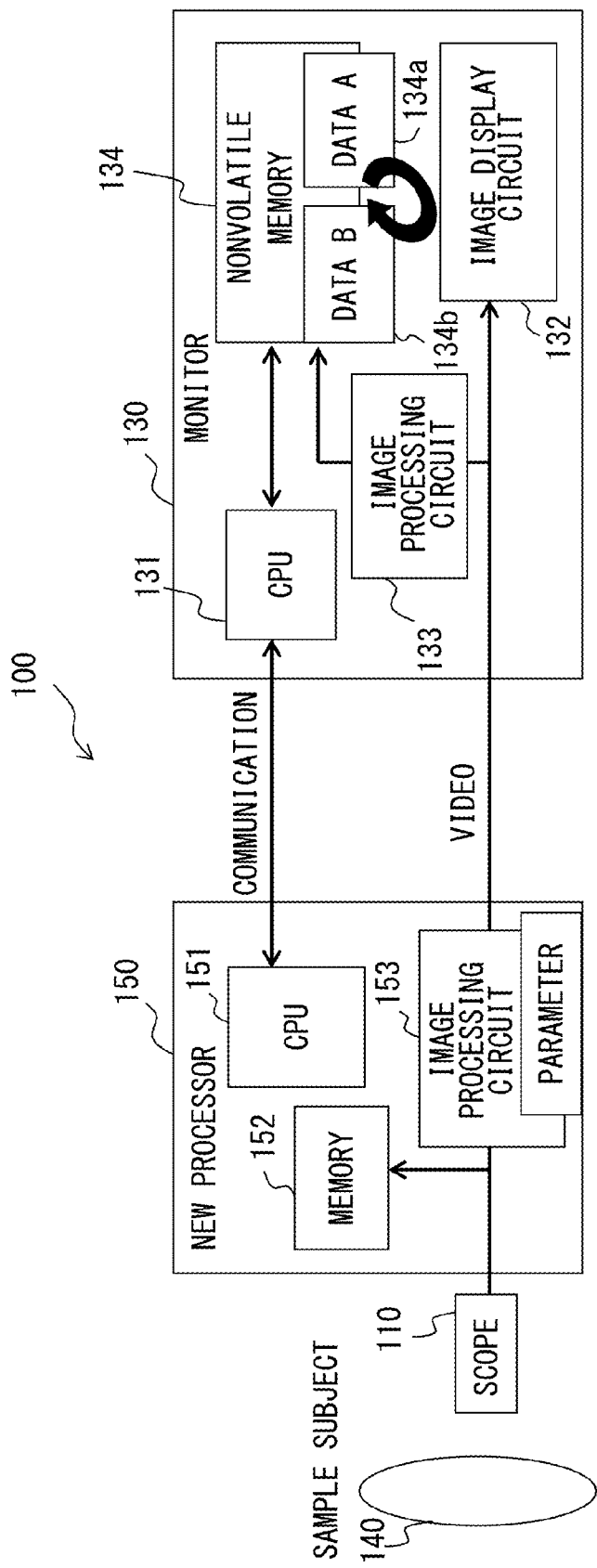
FIG. 2 is a first diagram that illustrates an example of a configuration of the endoscopic system according to the first embodiment after replacement.
Figure 3:
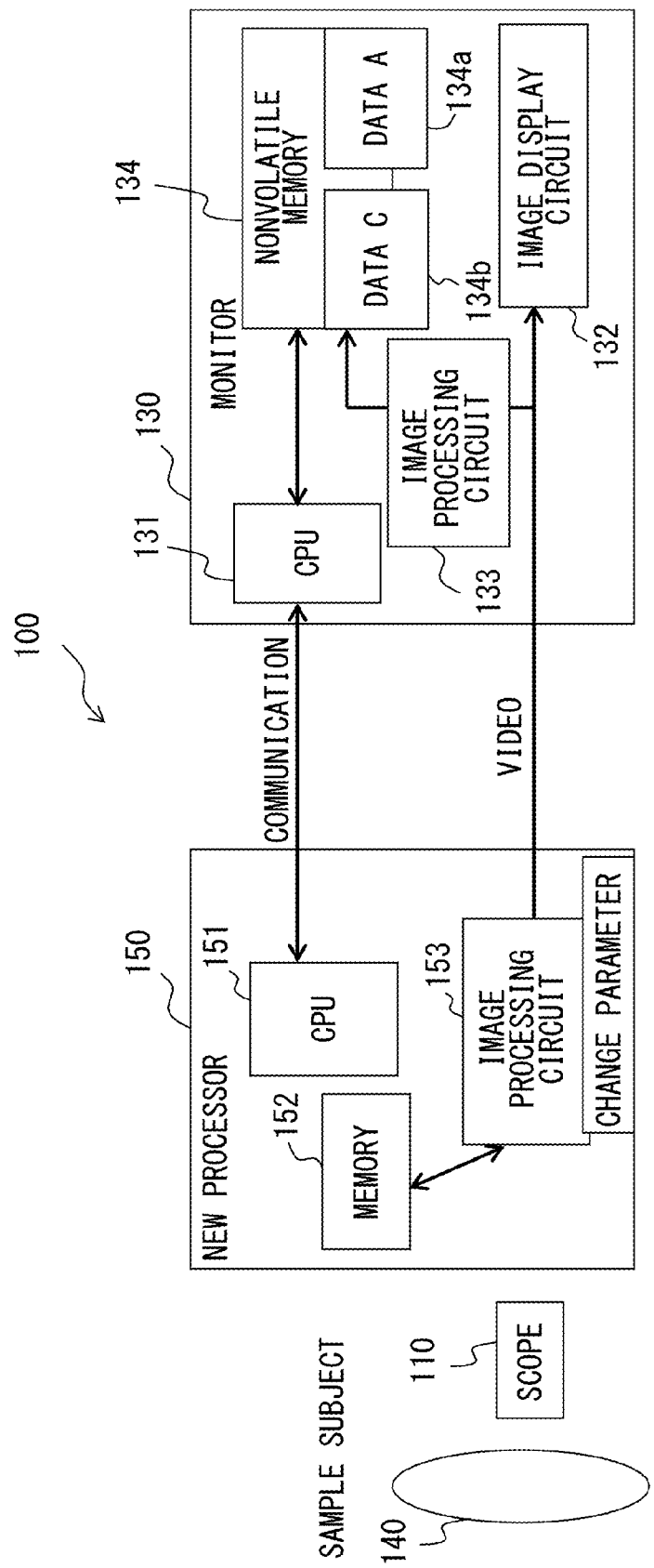
FIG. 3 is a second diagram that illustrates an example of a configuration of the endoscopic system according to the first embodiment after replacement.

FIG. 1 is a diagram that illustrates an example of a configuration of the endoscopic system according to the present embodiment before the old video processor is replaced with the new video processor (hereinafter simply referred to as "before replacement"). FIGS. 2 and 3 are diagrams that illustrate examples of configurations of the endoscopic system according to the present embodiment after the old video processor is replaced with the new video processor (hereinafter simply referred to as "after replacement"). Here, using these figures, the examples of configurations of the endoscopic system according to the present embodiment are described, and its operation is also described.

As illustrated in FIG. 1, an endoscopic system 100 according to the present embodiment before replacement includes a scope 110, an old video processor 120, and a monitor 130. The scope 110, the old video processor 120, and the monitor 130 are examples of an imaging device, an old image processing device, and a display device, respectively.

The scope 110 includes an imaging element such as a CCD (charge coupled device), and captures an image of a subject with the imaging element so as to obtain a subject image as an original image. For example, the scope 110 captures an image of a subject that is an observation target, so as to obtain an observation image as an original image. Further, for example, the scope 110 captures an image of a reference sample subject 140 so as to obtain a reference sample image as an original image. The reference sample subject 140 is an example of a reference subject, and is, for example, a predetermined color chart.

The old video processor 120 includes a CPU (central processing unit) 121 and an image processing circuit 122.

The CPU 121 controls the overall operation of the old video processor 120. Further, the CPU 121 performs various communications with a CPU 131 of the monitor 130.

With respect to an image obtained by the image element of the scope 110, the image processing circuit 122 performs image processing such as color-tone adjustment processing and brightness adjustment processing on the basis of a set image processing parameter. The set image processing parameter is an image processing parameter that is preset as a default, or an image processing parameter that is set by a user (such as a doctor or a nurse) through a manipulation unit (not shown) of the old video processor 120. Setting an image processing parameter also refers to performing an image processing setting, and changing the image processing parameter also refers to changing the image processing setting.

The monitor 130 includes the CPU 131, an image display circuit 132, an image processing circuit 133, and a nonvolatile memory 134.

The CPU 131 controls the overall operation of the monitor 130. Further, the CPU 131 performs various communications with the CPU 121 of the old video processor 120.

The image display circuit 132 displays, on a display unit (not shown), an image corresponding to a video signal of an image on which image processing is performed by the image processing circuit 122 of the old video processor 120 and that is input to the monitor 130.

On the basis of a video signal of a reference sample image on which image processing is performed by the image processing circuit 122 of the old video processor 120 and that is input to the monitor 130, the image processing circuit 133 obtains image information (RGB information and brightness information) on the reference sample image.

The nonvolatile memory 134 includes a first storage area 134a and a second storage area 134b; the latter will be described later. Image information on a reference sample image before replacement is stored in the first storage area 134a of the nonvolatile memory 134, the image information being obtained by the image processing circuit 133. The first storage area 134a of the nonvolatile memory 134 is an example of a first storage.

The endoscopic system 100 before replacement that has the configuration described above performs the following operation.

For example, during endoscopy, the imaging element of the scope 110 captures an image of a subject that is an observation target, so as to obtain an observation image as an original image. Next, with respect to the observation image, the image processing circuit 122 of the old video processor 120 performs image processing such as color-tone adjustment processing and brightness adjustment processing on the basis of a set image processing parameter. The image processing parameter that is set at this point is, for example, an image processing parameter that is set by a user so that an observation image in a proper color tone can be obtained. Then, the image display circuit 132 of the monitor 130 displays, on the display unit (not shown), an image corresponding to a video signal of the observation image on which image processing is performed by the image processing circuit 122 and that is input to the monitor 130.

For example, the following operation is performed just before the old video processor 120 is replaced with the new video processor 150. First, the imaging element of the scope 110 captures an image of the reference sample subject 140 so as to obtain a reference sample image as an original image. Next, with respect to the reference sample image, the image processing circuit 122 of the old video processor 120 performs image processing such as color-tone adjustment processing and brightness adjustment processing on the basis of a set image processing parameter. The image processing parameter that is set at this point remains the image processing parameter that is set during endoscopy. Next, on the basis of a video signal of the reference sample image on which image processing is performed by the image processing circuit 122 and that is input to the monitor 130, the image processing circuit 133 of the monitor 130 obtains image information on the reference sample image. Then, the image information on the reference sample image (the reference sample image before replacement) is stored in the first storage area 134a of the nonvolatile memory 134 (see "DATA A" of FIG. 1).

On the other hand, as illustrated in FIGS. 2 and 3, the endoscopic system 100 according to the present embodiment after replacement has a configuration in which the old video processor 120 has been replaced with the new video processor 150. The new video processor 150 is an example of a new image processing device.

The new video processor 150 includes a CPU 151, a memory 152, and an image processing circuit 153.

The CPU 151 controls the overall operation of the new video processor 150. Further, the CPU 151 performs various communications with the CPU 131 of the monitor 130. For example, the CPU 151 changes, according to an instruction from the CPU 131 to change an image processing parameter, the image processing parameter that is set in the image processing circuit 153.

A reference sample image obtained by the imaging element of the scope 110 is stored in the memory 152.

With respect to an image obtained by the image element of the scope 110, or with respect to a reference sample image read from the memory 152, the image processing circuit 153 performs image processing such as color-tone adjustment processing and brightness adjustment processing on the basis of a set image processing parameter. The set image processing parameter is an image processing parameter that is preset as a default. Or, the set image processing parameter is an image processing parameter that is set by a user through a manipulation unit (not shown) of the new video processor 150. Or, the set image processing parameter is an image processing parameter obtained by the change performed by the CPU 151 according to a change instruction from the CPU 131 of the monitor 130.

In principle, in the endoscopic system 100 after replacement, the scope 110 performs processing similar to the processing performed before replacement, but each unit included in the monitor 130 further performs the following processing.

The image display circuit 132 displays, on the display unit (not shown), an image corresponding to a video signal of an image on which image processing is performed by the image processing circuit 153 of the new video processor 150 and that is input to the monitor 130.

On the basis of a video signal of a reference sample image on which image processing is performed by the image processing circuit 153 of the new video processor 150 and that is input to the monitor 130, the image processing circuit 133 obtains image information (RGB information and brightness information) on the reference sample image.

Image information on a reference sample image after replacement is stored in the second storage area 134b of the nonvolatile memory 134, the image information being obtained by the image processing circuit 133. The second storage area 134b of the nonvolatile memory 134 is an example of a second storage.

The CPU 131 performs various communications with the CPU 151 of the new video processor 150. Further, the CPU 131 compares the image information on a reference sample image before replacement that is stored in the first storage area 134a of the nonvolatile memory 134 with the image information on a reference sample image after replacement that is stored in the second storage area 134b of the nonvolatile memory 134. Then, on the basis of a result of the comparison, the CPU 131 instructs the CPU 151 of the new video processor 150 to change an image processing parameter, such that the image information on a reference sample image after replacement that is stored in the second storage area 134b of the nonvolatile memory 134 is the same or substantially the same as the image information on a reference sample image before replacement that is stored in the first storage area 134a of the nonvolatile memory 134. The CPU 131 is an example of a comparison unit. Further, the CPU 151 changes the image processing parameter of the image processing circuit 153 according to the instruction from the CPU 131 to change an image processing parameter, so the CPU 131 actually changes the image processing parameter of the image processing circuit 153, and is also an example of a setting changing unit.

The endoscopic system 100 after replacement that has the configuration described above performs the following operation.

For example, just after the old video processor 120 is replaced with the new video processor 150, first, the imaging element of the scope 110 captures an image of the reference sample subject 140 so as to obtain a reference sample image as an original image. Next, the reference sample image is stored in the memory 152 of the new video processor 150 and is input to the image processing circuit 153 of the new video processor 150. With respect to the reference sample image, the image processing circuit 153 to which the reference sample image has been input performs image processing such as color-tone adjustment processing and brightness adjustment processing on the basis of a set image processing parameter. The image processing parameter that is set at this point is an image processing parameter that is set as a default because it is just after replacement. Next, on the basis of a video signal of the reference sample image on which image processing is performed by the image processing circuit 153 and that is input to the monitor 130, the image processing circuit 133 of the monitor 130 obtains image information on the reference sample image. Then, the image information on the reference sample image (the reference sample image after replacement) is stored in the second storage area 134b of the nonvolatile memory 134 (see "DATA B" of FIG. 2). Next, the CPU 131 compares the image information on a reference sample image before replacement that is stored in the first storage area 134a of the nonvolatile memory 134 with the image information on a reference sample image after replacement that is stored in the second storage area 134b of the nonvolatile memory 134. When CPU 131 determines, on the basis of a result of the comparison, that they are different (not the same or not substantially the same), the CPU 131 instructs the CPU 151 of the new video processor 150 to change an image processing parameter, such that the image information on a reference sample image after replacement that is stored in the second storage area 134b of the nonvolatile memory 134 is the same or substantially the same as the image information on a reference sample image before replacement that is stored in the first storage area 134a of the nonvolatile memory 134. When CPU 131 determines, as the result of the comparison described above, that they are the same or substantially the same, the CPU 131 does not give such an instruction to change an image processing parameter. The CPU 151 of the new video processor 150 that has received the instruction to change an image processing parameter changes the image processing parameter set in the image processing circuit 153 according to the change instruction. Next, with respect to the reference sample image read from the memory 152, the image processing circuit 153 performs image processing such as color-tone adjustment processing and brightness adjustment processing on the basis of a set image processing parameter after the change (see "CHANGE PARAMETER" of FIG. 3). Next, on the basis of a video signal of the reference sample image on which image processing is performed by the image processing circuit 153 and that is input to the monitor 130, the image processing circuit 133 of the monitor 130 obtains image information on the reference sample image. Then, the image information on the reference sample image (the reference sample image after replacement) is stored (overwritten) in the second storage area 134b of the nonvolatile memory 134 (see DATA C" of FIG. 3). After that, the above-described processing performed by the CPU 131, the CPU 151, the image processing circuit 153, and the image processing circuit 133 is performed repeatedly until the image information on a reference sample image after replacement that is stored in the second storage area 134b of the nonvolatile memory 134 becomes the same or substantially the same as the image information on a reference sample image before replacement that is stored in the first storage area 134a of the nonvolatile memory 134.

Figure 4:
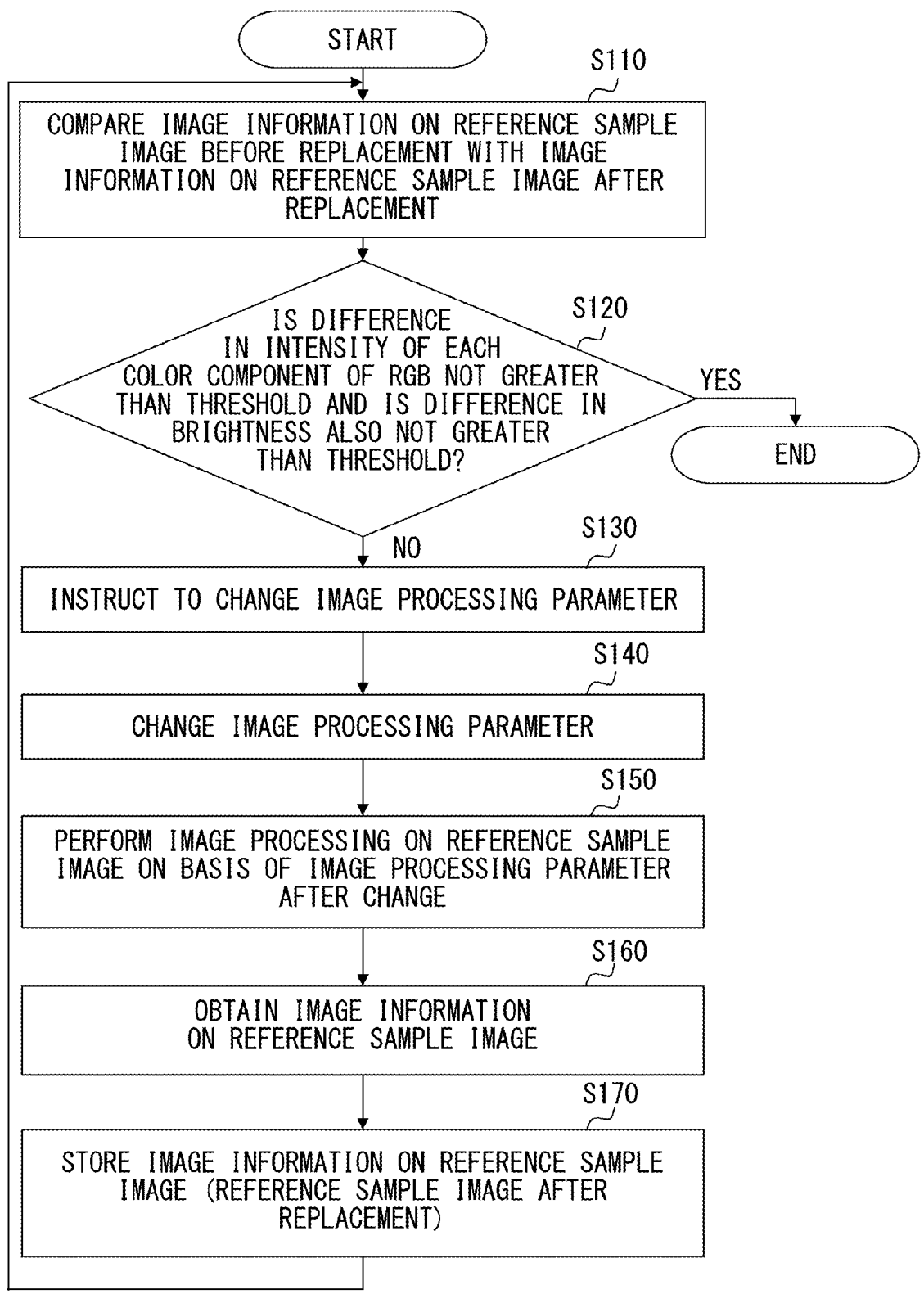
FIG. 4 is an exemplary flowchart that illustrates processing performed repeatedly in the endoscopic system according to the first embodiment after replacement.

The processing that is performed repeatedly is represented by, for example, the flowchart illustrated in FIG. 4.

As illustrated in FIG. 4, in the repeatedly performed processing, first, the CPU 131 of the monitor 130 compares image information on a reference sample image before replacement that is stored in the first storage area 134a of the nonvolatile memory 134 with image information on a reference sample image after replacement that is stored in the second storage area 134b of the nonvolatile memory 134 (S110).

Next, the CPU 131 determines whether a difference in intensity of each color component of the RGB between each pixel of the image information on a reference sample image before replacement and a corresponding pixel of the image information on a reference sample image after replacement is not greater than a threshold (for example, 1%) and whether a difference in brightness between them is also not greater than the threshold (for example, 1%) (S120). The differences are those between image information on a reference sample image before replacement and image information on a reference sample image after replacement. The threshold is a value that makes it possible to determine whether both of the pieces of image information are the same or substantially the same, and can be set (changed) discretionally by a user through a manipulation unit (not shown) of the monitor 130. For example, when the threshold is set to 1%, if a difference in intensity of a color component of R is not greater than 1%, this means that the difference in intensity of a color component of R is not greater than 1% of an intensity of a color component of R of a corresponding pixel of the reference sample image before replacement.

In the determination performed in S120, when Yes is obtained as a determination result, the repeatedly performed processing is terminated.

On the other hand, when No is obtained as the determination result in S120, the CPU 131 instructs the CPU 151 of the new video processor 150 to change an image processing parameter, such that the difference in intensity of each color component of the RGB between each pixel of the image information on a reference sample image before replacement and a corresponding pixel of the image information on a reference sample image after replacement is not greater than the threshold and such that the difference in brightness between them is also not greater than the threshold (S130). For example, with respect to a set of corresponding pixels of both of the pieces of image information, when the intensity of a color component of R of a reference sample image after replacement is stronger (or weaker) than the intensity of a color component of R of a reference sample image before replacement, an instruction to change an image processing parameter is given such that the intensity of a color component of R of the corresponding pixel of the reference sample image after replacement is made weaker (or stronger) than at present. Further, for example, with respect to a set of corresponding pixels of both of the pieces of image information, when the brightness of a reference sample image after replacement is stronger (or weaker) than the brightness of a reference sample image before replacement, an instruction to change an image processing parameter is given such that the brightness of the corresponding pixel of the reference sample image after replacement is made weaker (or stronger) than at present.

Next, the CPU 151 that has received the instruction to change an image processing parameter changes, according to the change instruction, the image processing parameter set in the image processing circuit 153 (S140).

Next, with respect to the reference sample image read from the memory 152, the image processing circuit 153 performs image processing such as color-tone adjustment processing and brightness adjustment processing on the basis of a set image processing parameter after the change (S150).

Next, on the basis of a video signal of the reference sample image on which image processing is performed by the image processing circuit 153 and that is input to the monitor 130, the image processing circuit 133 of the monitor 130 obtains image information on the reference sample image. (S160).

Then, the image information on the reference sample image (the reference sample image after replacement) is stored (overwritten) in the second storage area 134b of the nonvolatile memory 134 (S170), and the process returns to S110.

As a result of the above-described operation of the endoscopic system 100 just after replacement, an image processing parameter that permits obtaining of an image in a color tone that is similar to before replacement is automatically set in the image processing circuit 153 of the new video processor 150. Thus, the user does not have to perform an image processing setting of the new video processor 150.

Further, the following operation is performed during a subsequent endoscopy. First, the imaging element of the scope 110 captures an image of a subject that is an observation target, so as to obtain an observation image as an original image. Next, with respect to the observation image, the image processing circuit 153 of the new video processor 150 performs image processing such as color-tone adjustment processing and brightness adjustment processing on the basis of a set image processing parameter. The image processing parameter that is set at this point is an image processing parameter that is set in the image processing circuit 153 by the above-described operation of the endoscopic system 100 just after replacement. Then, the image display circuit 132 of the monitor 130 displays, on the display unit (not shown), an image corresponding to a video signal of the observation image on which image processing is performed by the image processing circuit 153 and that is input to the monitor 130.

According to the above-described operation of the endoscopic system 100 during subsequent endoscopy, a user can also observe, in endoscopy after replacement, an image in a color tone that is similar to before replacement.

As described above, the endoscopic system 100 according to the present embodiment makes it possible to eliminate the burden placed on a user when an image processing setting is performed upon replacing a video processor, and to also observe, in endoscopy after replacement, an image in a color tone that is similar to before replacement.

Second Embodiment

A medical system according to a second embodiment of the present invention is an endoscopic system.

The endoscopic system according to the present embodiment includes a new video processor and an old video processor that have a respective new and old relationship relative to each other as a video processor, and a scope, a monitor, and an external storage that are connected to the old video processor or the new video processor.

In an operation of the endoscopic system according to the present embodiment, the old video processor that is used along with the scope, the monitor, and the external storage is replaced with the new video processor due to, for example, a new purchase.

Figure 6:
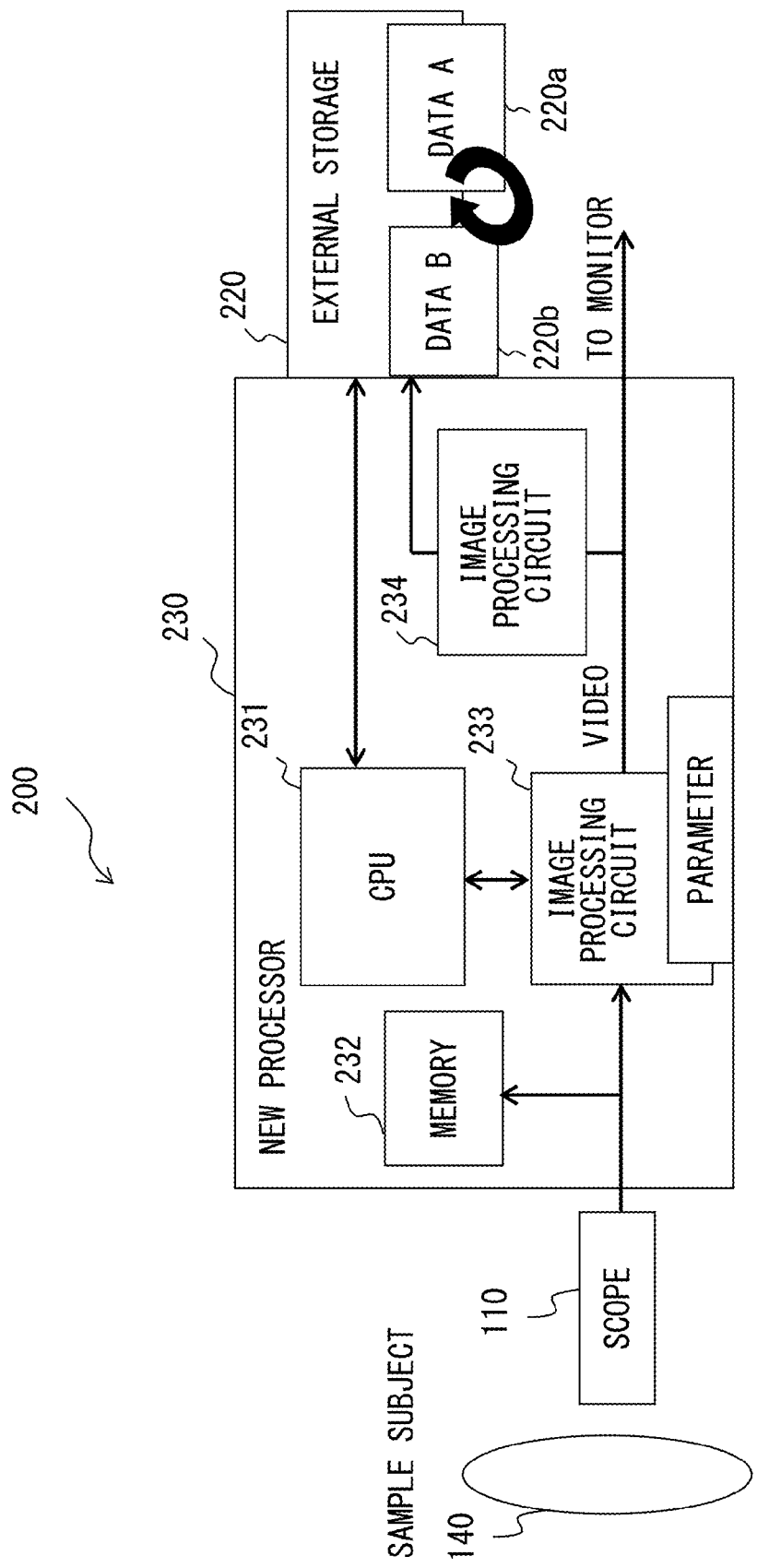
FIG. 6 is a first diagram that illustrates an example of a configuration of the endoscopic system according to the second embodiment after replacement.
Figure 7:
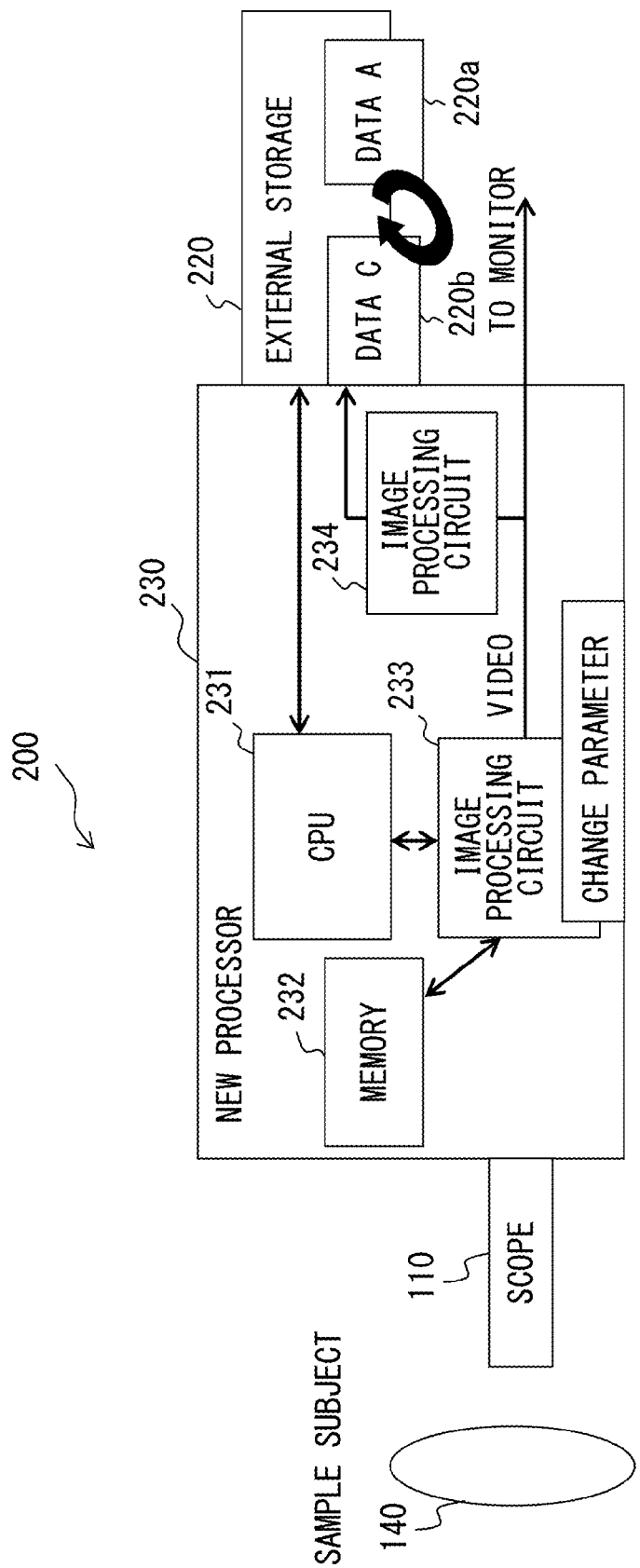
FIG. 7 is a second diagram that illustrates an example of a configuration of the endoscopic system according to the second embodiment after replacement.

FIG. 5 is a diagram that illustrates an example of a configuration of the endoscopic system according to the present embodiment before replacement. FIGS. 6 and 7 are diagrams that illustrate examples of configurations of the endoscopic system according to the present embodiment after replacement. Here, using these figures, the examples of configurations of the endoscopic system according to the present embodiment are described, and its operation is also described.

As illustrated in FIG. 5, an endoscopic system 200 according to the present embodiment before replacement includes the scope 110, an old video processor 210, an external storage 220, and a monitor (not shown). The old video processor 210 and the monitor (not shown) are examples of an old image processing device and a display device, respectively.

The scope 110 is as described in the first embodiment, so its description is omitted.

The old video processor 210 includes a CPU 211, an image processing circuit 212, and an image processing circuit 213.

The CPU 211 controls the overall operation of the old video processor 210, and also controls the operation of the external storage 220.

With respect to an image obtained by the image element of the scope 110, the image processing circuit 212 performs image processing such as color-tone adjustment processing and brightness adjustment processing on the basis of a set image processing parameter. The set image processing parameter is an image processing parameter that is preset as a default, or an image processing parameter that is set by a user through a manipulation unit (not shown) of the old video processor 210.

On the basis of a video signal of a reference sample image on which image processing is performed by the image processing circuit 212 and that is input to the monitor (not shown), the image processing circuit 213 obtains image information (RGB information and brightness information) on the reference sample image. The image processing circuit 213 corresponds to the image processing circuit 133 of the monitor 130 described in the first embodiment.

Image information on a reference sample image before replacement is stored in a first storage area 220a included in the external storage 220, the image information being obtained by the image processing circuit 213. The first storage area 220a of the external storage 220 is an example of a first storage, and corresponds to the first storage area 134a of the nonvolatile memory 134 described in the first embodiment.

The endoscopic system 200 before replacement that has the configuration described above performs the following operation.

For example, during endoscopy, the imaging element of the scope 110 captures an image of a subject that is an observation target, so as to obtain an observation image as an original image. Next, with respect to the observation image, the image processing circuit 212 of the old video processor 210 performs image processing such as color-tone adjustment processing and brightness adjustment processing on the basis of a set image processing parameter. The image processing parameter that is set at this point is, for example, an image processing parameter that is set by a user so that an observation image in a proper color tone can be obtained. Then, the monitor (not shown) displays an image corresponding to a video signal of the observation image on which image processing is performed by the image processing circuit 212.

For example, the following operation is performed just before the old video processor 210 is replaced with the new video processor 230. First, the imaging element of the scope 110 captures an image of the reference sample subject 140 so as to obtain a reference sample image as an original image. Next, with respect to the reference sample image, the image processing circuit 212 of the old video processor 210 performs image processing such as color-tone adjustment processing and brightness adjustment processing on the basis of a set image processing parameter. The image processing parameter that is set at this point is the image processing parameter that is set during endoscopy. Next, on the basis of a video signal of the reference sample image on which image processing is performed by the image processing circuit 212 and that is input to the monitor (not shown), the image processing circuit 213 obtains image information on the reference sample image. Then, the image information on the reference sample image (the reference sample image before replacement) is stored in the first storage area 220*a* of the external storage 220 (see "DATA A" of FIG. 5).

On the other hand, as illustrated in FIGS. 6 and 7, the endoscopic system 200 according to the present embodiment after replacement has a configuration in which the old video processor 210 has been replaced with the new video processor 230. The new video processor 230 is an example of a new image processing device.

The new video processor 230 includes a CPU 231, a memory 232, an image processing circuit 233, and an image processing circuit 234.

A reference sample image obtained by the imaging element of the scope 110 is stored in the memory 232. The memory 232 corresponds to the memory 152 of the new video processor 150 described in the first embodiment.

With respect to an image obtained by the image element of the scope 110, or with respect to a reference sample image read from the memory 232, the image processing circuit 233 performs image processing such as color-tone adjustment processing and brightness adjustment processing on the basis of a set image processing parameter. The set image processing parameter is an image processing parameter that is preset as a default. Or, the set image processing parameter is an image processing parameter that is set by a user through a manipulation unit (not shown) of the new video processor 230. Or, the set image processing parameter is an image processing parameter obtained by the change performed by the CPU 231. The image processing circuit 233 corresponds to the image processing circuit 153 of the new video processor 150 described in the first embodiment.

On the basis of a video signal of a reference sample image on which image processing is performed by the image processing circuit 233 and that is input to the monitor (not shown), the image processing circuit 234 obtains image information (RGB information and brightness information) on the reference sample image. The image processing circuit 234 is similar to the image processing circuit 213 of the old video processor 210, and corresponds to the image processing circuit 133 of the monitor 130 described in the first embodiment.

Image information on a reference sample image after replacement is stored in the second storage area 220*b* included in the external storage 220, the image information being obtained by the image processing circuit 234. The second storage area 220*b* of the external storage 220 is an example of a second storage, and corresponds to the second storage area 134*b* of the nonvolatile memory 134 described in the first embodiment.

The CPU 231 controls the overall operation of the new video processor 230, and also controls the operation of the external storage 220. Further, the CPU 231 compares the image information on a reference sample image before replacement that is stored in the first storage area 220*a* of the external storage 220 with the image information on a reference sample image after replacement that is stored in the second storage area 220*b* of the external storage 220. Then, on the basis of a result of the comparison, the CPU 231 changes the image processing parameter of the image processing circuit 233 such that the image information on a reference sample image after replacement that is stored in the second storage area 220*b* of the external storage 220 is the same or substantially the same as the image information on a reference sample image before replacement that is stored in the first storage area 220*a* of the external storage 220. The CPU 231 is an example of a comparison unit and a setting changing unit.

The endoscopic system 200 after replacement that has the configuration described above performs the following operation.

For example, just after the old video processor 210 is replaced with the new video processor 230, first, the imaging element of the scope 110 captures an image of the reference sample subject 140 so as to obtain a reference sample image as an original image. Next, the reference sample image is stored in the memory 232 of the new video processor 230 and is input to the image processing circuit 233 of the new video processor 230. With respect to the reference sample image, the image processing circuit 233 to which the reference sample image has been input performs image processing such as color-tone adjustment processing and brightness adjustment processing on the basis of a set image processing parameter. The image processing parameter that is set at this point is an image processing parameter that is set as a default because it is just after replacement. Next, on the basis of a video signal of the reference sample image on which image processing is performed by the image processing circuit 233 and that is input to the monitor (not shown), the image processing circuit 234 obtains image information on the reference sample image. Then, the image information on the reference sample image (the reference sample image after replacement) is stored in the second storage area 220*b* of the external storage 220 (see "DATA B" of FIG. 6). Next, the CPU 231 compares the image information on a reference sample image before replacement that is stored in the first storage area 220*a* of the external storage 220 with the image information on a reference sample image after replacement that is stored in the second storage area 220*b* of the external storage 220. When CPU 231 determines, on the basis of a result of the comparison, that they are different (not the same or not substantially the same), the CPU 231 changes the image processing parameter set in the image processing circuit 233, such that the image information on a reference sample image after replacement that is stored in the second storage area 220*b* of the external storage 220 is the same or substantially the same as the image information on a reference sample image before replacement that is stored in the first storage area 220*a* of the external storage 220. When CPU 231 determines, as the result of the comparison described above, that they are the same or substantially the same, the CPU 231 does not perform such a change in an image processing parameter. Next, when the change in an image processing parameter is performed by the CPU 231, with respect to the reference sample image read from the memory 232, the image processing circuit 233 performs image processing such as color-tone adjustment processing and brightness adjustment processing on the basis of a set image processing parameter after the change (see "CHANGE PARAMETER" of FIG. 7). Next, on the basis of a video signal of the reference sample image on which image processing is performed by the image processing circuit 233 and that is input to the monitor (not shown), the image processing circuit 234 obtains image information on the reference sample image. Then, the image information on the reference sample image (the reference sample image after replacement) is stored (overwritten) in the second storage area 220*b* of the external storage 220 (see "DATA C" of FIG. 7). After that, the above-described processing performed by the CPU 231, the image processing circuit 233, and the image processing circuit 234 is performed repeatedly until the image information on a reference sample image after replacement that is stored in the second storage area 220b of the external storage 220 becomes the same or substantially the same as the image information on a reference sample image before replacement that is stored in the first storage area 220a of the external storage 220.

In principle, this repeatedly performed processing described above is similarly represented by the flowchart illustrated in FIG. 4, except that a unit that performs the processing, a location for storing a reference sample image, and a location for storing pieces of image information on reference sample images before and after replacement are different. Specifically, in the present embodiment, the unit that performs the processes of S110 to S140 of FIG. 4 is the CPU 231 of the new video processor 230. In this case, the threshold used to perform the determination in S120 can be set (changed) discretionally by a user through, for example, a manipulation unit (not shown) of the new video processor 230. In the present embodiment, the unit that performs the process of S150 is the image processing circuit 233 of the new video processor 230. In the present embodiment, the unit that performs the process of S160 is the image processing circuit 234 of the new video processor 230. In the present embodiment, the reference sample image is stored in the memory 232 of the new video processor 230. In the present embodiment, the pieces of image information on reference sample images before replacement and after replacement are respectively stored in the first storage area 220a and the second storage area 220b of the external storage 220. In principle, the other points are similarly represented by the flowchart illustrated in FIG. 4. Thus, the detailed description of the repeatedly performed processing is omitted.

As a result of the above-described operation of the endoscopic system 200 just after replacement, an image processing parameter that permits obtaining of an image in a color tone that is similar to before replacement is automatically set in the image processing circuit 233 of the new video processor 230. Thus, the user does not have to perform an image processing setting of the new video processor 230.

Further, the following operation is performed during subsequent endoscopy. First, the imaging element of the scope 110 captures an image of a subject that is an observation target, so as to obtain an observation image as an original image. Next, with respect to the observation image, the image processing circuit 233 of the new video processor 230 performs image processing such as color-tone adjustment processing and brightness adjustment processing on the basis of a set image processing parameter. The image processing parameter that is set at this point is an image processing parameter that is set in the image processing circuit 233 by the above-described operation of the endoscopic system 200 just after replacement. Then, the monitor (not shown) displays an image corresponding to a video signal of the observation image on which image processing is performed by the image processing circuit 233.

According to the above-described operation of the endoscopic system 200 during subsequent endoscopy, a user can also observe, after replacement, an image in a color tone that is similar to before replacement.

As described above, the endoscopic system 200 according to the present embodiment makes it possible to eliminate the burden placed on a user when an image processing setting is performed upon replacing a video processor, and to also observe, in endoscopy after replacement, an image in a color tone that is similar to before replacement, as in the first embodiment.

Third Embodiment

A medical system according to a third embodiment of the present invention is an endoscopic system.

As in the first embodiment, the endoscopic system according to the present embodiment includes a new video processor and an old video processor that have a respective new and old relationship relative to each other as a video processor, and a scope and a monitor that are connected to the old video processor or the new video processor.

As in the first embodiment, in an operation of the endoscopic system according to the present embodiment, the old video processor that is used along with the scope and the monitor is replaced with the new video processor due to, for example, a new purchase.

Figure 8:
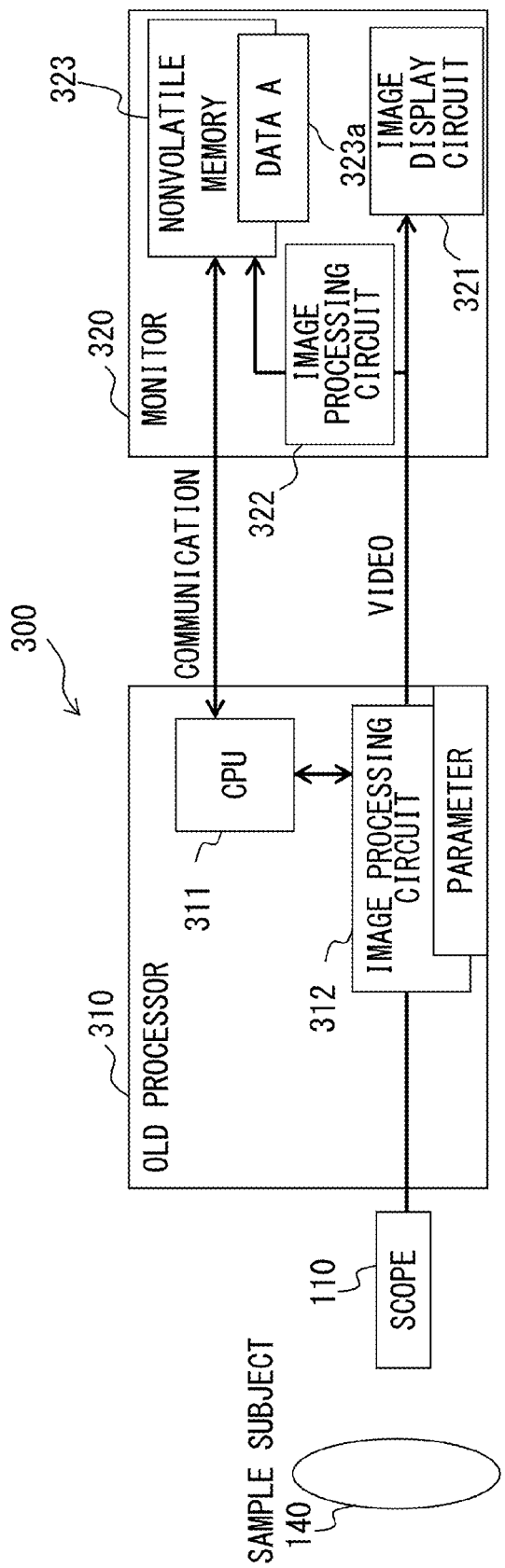
FIG. 8 is a diagram that illustrates an example of a configuration of an endoscopic system according to a third embodiment before replacement.
Figure 9:
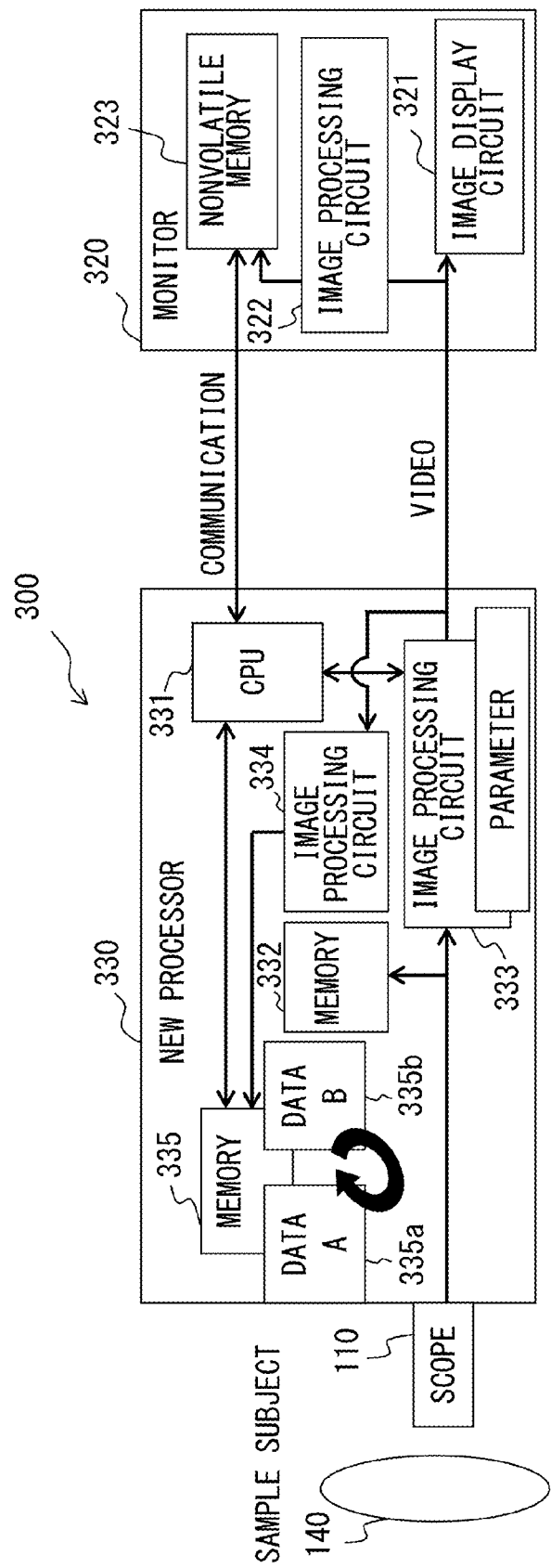
FIG. 9 is a first diagram that illustrates an example of a configuration of the endoscopic system according to the third embodiment after replacement.
Figure 10:
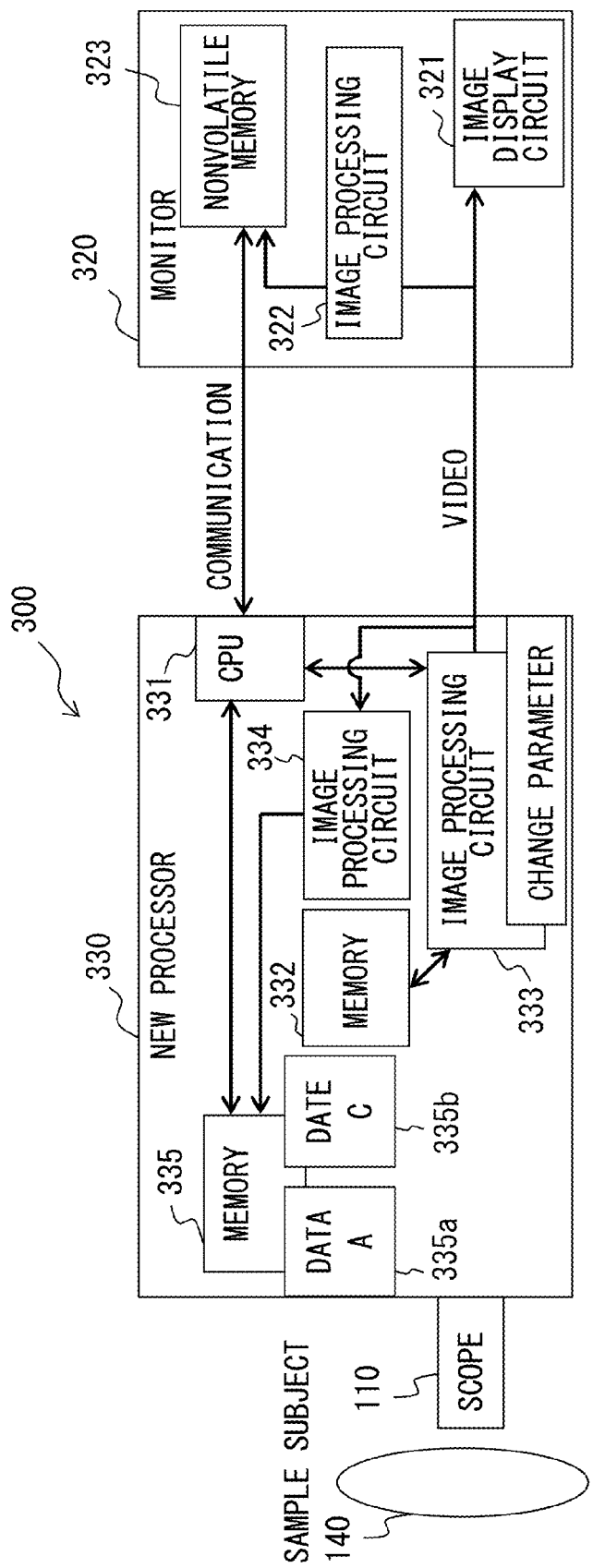
FIG. 10 is a second diagram that illustrates an example of a configuration of the endoscopic system according to the third embodiment after replacement.

FIG. 8 is a diagram that illustrates an example of a configuration of the endoscopic system according to the present embodiment before replacement. FIGS. 9 and 10 are diagrams that illustrate examples of configurations of the endoscopic system according to the present embodiment after replacement. Here, using these figures, the examples of configurations of the endoscopic system according to the present embodiment are described, and its operation is also described.

As illustrated in FIG. 8, an endoscopic system 300 according to the present embodiment before replacement includes the scope 110, an old video processor 310, and a monitor 320. The old video processor 310 and the monitor 320 are examples of an old image processing device and a display device, respectively.

The scope 110 is as described in the first embodiment, so its description is omitted.

The old video processor 310 includes a CPU 311 and an image processing circuit 312.

The CPU 311 controls the overall operation of the old video processor 310, and also controls a nonvolatile memory 323 of the monitor 320.

With respect to an image obtained by the image element of the scope 110, the image processing circuit 312 performs image processing such as color-tone adjustment processing and brightness adjustment processing on the basis of a set image processing parameter. The set image processing parameter is an image processing parameter that is preset as a default, or an image processing parameter that is set by a user through a manipulation unit (not shown) of the old video processor 310. The image processing circuit 312 corresponds to the image processing circuit 122 of the old video processor 120 described in the first embodiment.

The monitor 320 includes an image display circuit 321, an image processing circuit 322, and the nonvolatile memory 323.

The image display circuit 321 displays, on a display unit (not shown), an image corresponding to a video signal of an image on which image processing is performed by the image processing circuit 312 of the old video processor 310 and that is input to the monitor 320. The image display circuit 321 corresponds to the image display circuit 132 of the monitor 130 described in the first embodiment.

On the basis of a video signal of a reference sample image on which image processing is performed by the image processing circuit 312 of the old video processor 310 and that is input to the monitor 320, the image processing circuit 322 obtains image information (RGB information and brightness information) on the reference sample image. The image processing circuit 322 corresponds to the image processing circuit 133 of the monitor 130 described in the first embodiment.

The nonvolatile memory 323 includes a first storage area 323a. Image information on a reference sample image before replacement is stored in the first storage area 323a, the image information being obtained by the image processing circuit 322.

The endoscopic system 300 before replacement that has the configuration described above performs the following operation.

For example, during endoscopy, the imaging element of the scope 110 captures an image of a subject that is an observation target, so as to obtain an observation image as an original image. Next, with respect to the observation image, the image processing circuit 312 of the old video processor 310 performs image processing such as color-tone adjustment processing and brightness adjustment processing on the basis of a set image processing parameter. The image processing parameter that is set at this point is, for example, an image processing parameter that is set by a user so that an observation image in a proper color tone can be obtained. Then, the image display circuit 321 of the monitor 320 displays, on the display unit (not shown), an image corresponding to a video signal of the observation image on which image processing is performed by the image processing circuit 312 and that is input to the monitor 320.

For example, the following operation is performed just before the old video processor 310 is replaced with the new video processor 330. First, the imaging element of the scope 110 captures an image of the reference sample subject 140 so as to obtain a reference sample image as an original image. Next, with respect to the reference sample image, the image processing circuit 312 of the old video processor 310 performs image processing such as color-tone adjustment processing and brightness adjustment processing on the basis of a set image processing parameter. The image processing parameter that is set at this point is the image processing parameter that is set during endoscopy. Next, on the basis of a video signal of the reference sample image on which image processing is performed by the image processing circuit 312 and that is input to the monitor 320, the image processing circuit 322 of the monitor 320 obtains image information on the reference sample image. Then, the image information on the reference sample image (the reference sample image before replacement) is stored in the first storage area 323a of the nonvolatile memory 323 (see "DATA A" of FIG. 8).

On the other hand, as illustrated in FIGS. 9 and 10, the endoscopic system 300 according to the present embodiment after replacement has a configuration in which the old video processor 310 has been replaced with the new video processor 330. The new video processor 330 is an example of a new image processing device.

The new video processor 330 includes a CPU 331, a memory 332, an image processing circuit 333, an image processing circuit 334, and a memory 335.

A reference sample image obtained by the imaging element of the scope 110 is stored in the memory 332. The memory 332 corresponds to the memory 152 of the new video processor 150 described in the first embodiment.

With respect to an image obtained by the image element of the scope 110, or with respect to a reference sample image read from the memory 332, the image processing circuit 333 performs image processing such as color-tone adjustment processing and brightness adjustment processing on the basis of a set image processing parameter. The set image processing parameter is an image processing parameter that is preset as a default. Or, the set image processing parameter is an image processing parameter that is set by a user through a manipulation unit (not shown) of the new video processor 330. Or, the set image processing parameter is an image processing parameter obtained by the change performed by the CPU 331. The image processing circuit 333 corresponds to the image processing circuit 153 of the new video processor 150 described in the first embodiment.

On the basis of a video signal of a reference sample image on which image processing is performed by the image processing circuit 333 and that is input to the monitor 320, the image processing circuit 334 obtains image information (RGB information and brightness information) on the reference sample image. The image processing circuit 334 is similar to the image processing circuit 322 of the monitor 320, and corresponds to the image processing circuit 133 of the monitor 130 described in the first embodiment.

The memory 335 includes a first storage area 335a and a second storage area 335b. Image information on a reference sample image before replacement is stored in the first storage area 335a of the memory 335, the image information being stored in the first storage area 323a of the nonvolatile memory 323 of the monitor 320. Further, image information on a reference sample image after replacement is stored in the second storage area 335b of the memory 335, the image information being obtained by the image processing circuit 334. The first storage area 335a of the memory 335 is an example of a first storage, and corresponds to the first storage area 134a of the nonvolatile memory 134 described in the first embodiment. Further, the second storage area 335b of the memory 335 is an example of a second storage, and corresponds to the second storage area 134b of the nonvolatile memory 134 described in the first embodiment.

The CPU 331 controls the overall operation of the new video processor 330, and also controls the nonvolatile memory 323 of the monitor 320. Further, the CPU 331 reads the image information on a reference sample image before replacement and stores the image information in the first storage area 335a of the memory 335, the image information being stored in the first storage area 323a of the nonvolatile memory 323. Furthermore, the CPU 331 compares the image information on a reference sample image before replacement that is stored in the first storage area 335a of the memory 335 with the image information on a reference sample image after replacement that is stored in the second storage area 335b of the memory 335. Then, on the basis of a result of the comparison, the CPU 331 changes the image processing parameter set in the image processing circuit 333, such that the image information on a reference sample image after replacement that is stored in the second storage area 335b of the memory 335 is the same or substantially the same as the image information on a reference sample image before replacement that is stored in the first storage area 335a of the memory 335. The CPU 331 is an example of a comparison unit and a setting changing unit.

In principle, in the endoscopic system 300 after replacement, the scope 110 performs processing similar to the processing performed before replacement, but the image display circuit 321 of the monitor 320 further performs the following processing.

The image display circuit 321 displays, on the display unit (not shown), an image corresponding to a video signal of an image on which image processing is performed by the image processing circuit 333 of the new video processor 330 and that is input to the monitor 320.

The endoscopic system 300 after replacement that has the configuration described above performs the following operation.

For example, just after the old video processor 310 is replaced with the new video processor 330, first, the CPU 331 of the new video processor 330 reads image information on a reference sample image before replacement and stores the image information in the first storage area 335a of the memory 335, the image information being stored in the first storage area 323a of the nonvolatile memory 323 of the monitor 320 (see "DATA A" of FIG. 9). Next, the imaging element of the scope 110 captures an image of the reference sample subject 140 so as to obtain a reference sample image as an original image. Next, the reference sample image is stored in the memory 332 of the new video processor 330, and is input to the image processing circuit 333 of the new video processor 330. With respect to the reference sample image, the image processing circuit 333 to which the reference sample image has been input performs image processing such as color-tone adjustment processing and brightness adjustment processing on the basis of a set image processing parameter. The image processing parameter that is set at this point is an image processing parameter that is set as a default because it is just after replacement. Next, on the basis of a video signal of the reference sample image on which image processing is performed by the image processing circuit 333 and that is input to the monitor 320, the image processing circuit 334 obtains image information on the reference sample image. Then, the image information on the reference sample image (the reference sample image after replacement) is stored in the second storage area 335b of the memory 335 (see "DATA B" of FIG. 9). Next, the CPU 331 compares the image information on a reference sample image before replacement that is stored in the first storage area 335a of the memory 335 with the image information on a reference sample image after replacement that is stored in the second storage area 335b of the memory 335. When the CPU 331 determines, on the basis of a result of the comparison, that they are different (not the same or not substantially the same), the CPU 331 changes the image processing parameter set in the image processing circuit 333, such that the image information on a reference sample image after replacement that is stored in the second storage area 335b of the memory 335 is the same or substantially the same as the image information on a reference sample image before replacement that is stored in the first storage area 335a of the memory 335. When the CPU 331 determines, as the result of the comparison described above, that they are the same or substantially the same, the CPU 331 does not perform such a change in an image processing parameter. Next, when the change in an image processing parameter is performed by the CPU 331, with respect to the reference sample image read from the memory 332, the image processing circuit 333 performs image processing such as color-tone adjustment processing and brightness adjustment processing on the basis of a set image processing parameter after the change (see "CHANGE PARAMETER" of FIG. 10). Next, on the basis of a video signal of the reference sample image on which image processing is performed by the image processing circuit 333 and that is input to the monitor 320, the image processing circuit 334 obtains image information on the reference sample image. Then, the image information on the reference sample image (the reference sample image after replacement) is stored (overwritten) in the second storage area 335b of the memory 335 (see "DATA C" of FIG. 10). After that, the above-described processing performed by the CPU 331, the image processing circuit 333, and the image processing circuit 334 is performed repeatedly until the image information on a reference sample image after replacement that is stored in the second storage area 335b of the memory 335 becomes the same or substantially the same as the image information on a reference sample image before replacement that is stored in the first storage area 335a of the memory 335.

In principle, this repeatedly performed processing described above is similarly represented by the flowchart illustrated in FIG. 4, except that a unit that performs the processing, a location for storing a reference sample image, and a location for storing pieces of image information on reference sample images before and after replacement are different. Specifically, in the present embodiment, the unit that performs the processes of S110 to S140 of FIG. 4 is the CPU 331 of the new video processor 330. In this case, the threshold used to perform the determination in S120 can be set (changed) discretionally by a user through, for example, a manipulation unit (not shown) of the new video processor 330. In the present embodiment, the unit that performs the process of S150 is the image processing circuit 333 of the new video processor 330. In the present embodiment, the unit that performs the process of S160 is the image processing circuit 334 of the new video processor 330. In the present embodiment, the reference sample image is stored in the memory 332 of the new video processor 330. In the present embodiment, the pieces of image information on reference sample images before replacement and after replacement are respectively stored in the first storage area 335a and the second storage area 335b of the memory 335. In principle, the other points are similarly represented by the flowchart illustrated in FIG. 4. Thus, the detailed description of the repeatedly performed processing is omitted.

As a result of the above-described operation of the endoscopic system 300 just after replacement, an image processing parameter that permits obtaining of an image in a color tone that is similar to before replacement is automatically set in the image processing circuit 333 of the new video processor 330. Thus, the user does not have to perform an image processing setting of the new video processor 330.

Further, the following operation is performed during subsequent endoscopy. First, the imaging element of the scope 110 captures an image of a subject that is an observation target, so as to obtain an observation image as an original image. Next, with respect to the observation image, the image processing circuit 333 of the new video processor 330 performs image processing such as color-tone adjustment processing and brightness adjustment processing on the basis of a set image processing parameter. The image processing parameter that is set at this point is an image processing parameter that is set in the image processing circuit 333 by the above-described operation of the endoscopic system 300 just after replacement. Then, the image display circuit 321 of the monitor 320 displays, on the display unit (not shown), an image corresponding to a video signal of the observation image on which image processing is performed by the image processing circuit 333 and that is input to the monitor 320.

According to the above-described operation of the endoscopic system 300 during subsequent endoscopy, a user can also observe, in endoscopy after replacement, an image in a color tone that is similar to before replacement.

As described above, the endoscopic system 300 according to the present embodiment makes it possible to eliminate the burden placed on a user when an image processing setting is performed upon replacing a video processor, and to also observe, after replacement, an image in a color tone that is similar to before replacement, as in the first embodiment.

Various modifications may be made to the above-described medical system according to the first to third embodiments.

Figure 11:
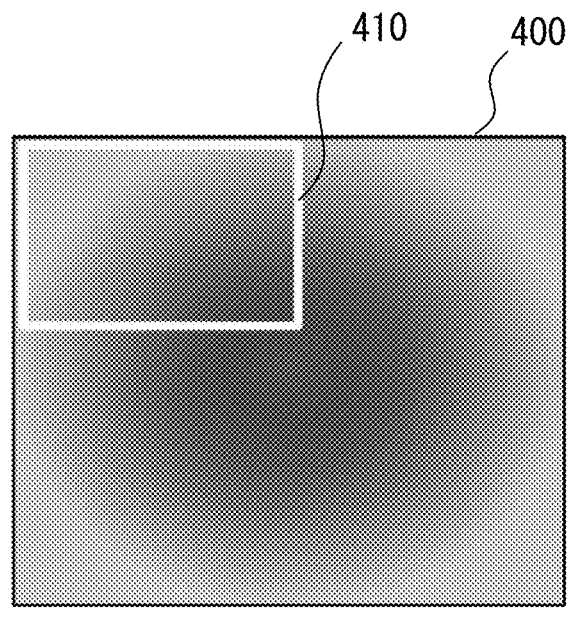
FIG. 11 illustrates an example of a specific area in a reference sample image.

For example, in the endoscopic system 100 according to the first embodiment, the image information on a reference sample image, which is obtained by the image processing circuit 133 of the monitor 130, may be image information about a certain area in the reference sample image, such as image information about a specific area 410 in a reference sample image 400 illustrated in FIG. 11. In this case, for example, the certain area may be determined on the basis of a pixel in a specific position in the reference sample image (for example, a pixel in first row and first column), or on the basis of a mark area, in the reference sample image, that corresponds to a mark put on the reference sample subject 140. Likewise, in the endoscopic system 200 according to the second embodiment, the pieces of image information on a reference sample image, which are obtained by the image processing circuit 213 of the old video processor 210 and by the image processing circuit 234 of the new video processor 230, may be pieces of image information about a certain area in the reference sample image. Likewise, in the endoscopic system 300 according to the third embodiment, the pieces of image information on a reference sample image, which are obtained by the image processing circuit 322 of the monitor 320 and by the image processing circuit 334 of the new video processor 330, may be pieces of image information about a certain area in the reference sample image.

For example, in endoscopic system 100 according to the first embodiment, the image processing circuit 133 of the monitor 130 obtains both RGB information and brightness information as image information, but it may only obtain, for example, one of the RGB information and the brightness information. Likewise, in the endoscopic system 200 according to the second embodiment, the image processing circuit 213 of the old video processor 210 and the image processing circuit 234 of the new video processor 230 may only obtain one of the RGB information and the brightness information. Likewise, in the endoscopic system 300 according to the third embodiment, the image processing circuit 322 of the monitor 320 and the image processing circuit 334 of the new video processor 330 may only obtain one of the RGB information and the brightness information. However, when these modifications are made, in S120 of FIG. 4, it is determined, according to the modification, whether a difference in intensity of each color component of the RGB is not greater than a threshold, or whether a difference in brightness is not greater than the threshold. Further, in S130 and S140 of FIG. 4, the image processing parameter is changed such that the difference in intensity of each color component of the RGB is not greater than the threshold, or such that the difference in brightness is not greater than the threshold.

For example, in the endoscopic system 100 according to the first embodiment, the old video processor 120 or the new video processor 150 may be configured to be connected to a network such as a LAN (local area network) in a hospital. Likewise, in the endoscopic system 200 according to the second embodiment, the old video processor 210 or the new video processor 230 may be configured to be connected to a network such as a LAN in a hospital. Likewise, in the endoscopic system 300 according to the third embodiment, the old video processor 310 or the new video processor 330 may be configured to be connected to a network such as a LAN in a hospital.

For example, a program that is executed by each CPU included in the endoscopic system according to each of the first to third embodiments may be stored in a ROM (read only memory) included in a device that includes the CPU, and the program may be temporarily stored in a RAM (random access memory) included in the device that includes the CPU so as to be executed by the CPU. Further, the device that includes the CPU may be connected to a network, and the program may be temporarily stored, from an external device connected to the network, in the RAM included in the device that includes the CPU so as to be executed by the CPU. Furthermore, the device that includes the CPU may include a medium reader, and the program may be temporality stored, from a portable recording medium set in the medium reader, in the RAM included in the device that includes the CPU so as to be executed by the CPU. In this case, as the portable recording medium, recording media in various forms such as a CD-ROM (compact disc read only memory), a flexible disk, an optical disk, a magnetic optical disk, a DVD (digital versatile disc), and a USE memory can be used.

In each of the first to third embodiments, an example of applying the present invention to an endoscopic system has been described, but it is also applicable to a medical system other than an endoscopic system if the system includes an imaging device, an image processing device, and a display device, or further includes an external storage in addition to those devices, in which the image processing device performs image processing on an image captured by the imaging device and the image is displayed on a monitor.

According to embodiments described above, it is possible to eliminate, upon replacing an old image processing device with a new image processing device, the burden placed on a user when an image processing setting is performed upon replacement, and to also observe, after replacement, an image in a color tone that is similar to before replacement.

The embodiments described above are just examples to facilitate understanding of the present invention, and the embodiment of the present invention is not limited to these embodiments. Various modifications and alterations may be made thereto without departing from the spirit of the invention specified in the claims.

What is claimed is:

1. A medical system that includes a first image processing device and a second image processing device that is different from the first image processing device, and an imaging device that is connected to the first image processing device or the second image processing device, the medical system comprising:
   a first storage that stores image information on an image that is obtained by the imaging device capturing an image of a reference subject and on which image processing is performed by the first image processing device;
   a second storage that stores image information on an image that is obtained by the imaging device capturing an image of the reference subject and on which image processing is performed by the second image processing device;
   a comparison unit that compares the image information stored in the first storage with the image information stored in the second storage; and
   a setting changing unit that changes an image processing setting of the second image processing device on the basis of a result of the comparison performed by the comparison unit, such that the image information stored in the second storage is identical or substantially identical to the image information stored in the first storage.

2. The medical system according to claim 1 further comprising a display device to which image information output from the first image processing device or the second image processing device is input, so as to display an image represented by the image information, wherein the first storage, the second storage, the comparison unit, and the setting changing unit are included in the display device.

3. The medical system according to claim 1 further comprising an external storage connected to the first image processing device or the second image processing device, wherein
the first storage is a first storage area of the external storage,
the second storage is a second storage area of the external storage, and
the comparison unit and the setting changing unit are included in the second image processing device.

4. The medical system according to claim 1, wherein the first storage, the second storage, the comparison unit and the setting changing unit are included in the second image processing device.

5. The medical system according to claim 1, wherein the image information is RGB information or intensity information of an image or both of the pieces of the image information.

6. A method for performing an image processing setting for a medical system that includes an imaging device that is connected to a first image processing device or a second image processing device that is different from the first image processing device, the method comprising:
a first image-capturing step of capturing, by the imaging device, an image of a reference subject;
a first image-processing step of performing, by the first image processing device, image processing on the image captured by the imaging device;
a first storing step of storing, in a first storage, image information on the image on which image processing is performed by the first image processing device and that is input to a display device;
a second image-capturing step of capturing, by the imaging device, an image of the reference subject;
a second image-processing step of performing, by the second image processing device, image processing on the image captured by the imaging device;
a second storing step of storing, in a second storage, image information on the image on which image processing is performed by the second image processing device and that is input to the display device;
a comparison step of comparing the image information stored in the first storage with the image information stored in the second storage; and
a change step of changing an image processing setting of the second image processing device on the basis of a result of the comparison such that the image information stored in the second storage is identical or substantially identical to the image information stored in the first storage, wherein
the second image-processing step, the second storing step, the comparison step, and the change step are performed repeatedly until a result of the comparison that the image information stored in the second storage and the image information stored in the first storage are identical or substantially identical is obtained.

7. An image processing device comprising:
a certain image processing unit that performs image processing on an image obtained by an imaging device capturing an image of a reference subject;
a first storage that stores image information on an image that is obtained by the imaging device capturing an image of the reference subject and on which image processing is performed by another image processing unit that is different from the certain image processing unit;
a second storage that stores image information on an image on which image processing is performed by the certain image processing unit;
a comparison unit that compares the image information stored in the first storage with the image information stored in the second storage; and
a setting changing unit that changes an image processing setting of the certain image processing unit such that the image information stored in the second storage is identical or substantially identical to the image information stored in the first storage.

* * * * *